United States Patent [19]

Kaluza et al.

[11] Patent Number: 5,354,669
[45] Date of Patent: Oct. 11, 1994

[54] TYPE II RESTRICTION ENDONUCLEASE SEXAI

[75] Inventors: Klaus Kaluza, Bad Heilbrunn; Johannes Auer; Bruno Frey, both of Penzberg, all of Fed. Rep. of Germany

[73] Assignee: Boehringer Mannheim GmbH, Mannheim, Fed. Rep. of Germany

[21] Appl. No.: 94,374

[22] Filed: Jul. 19, 1993

[30] Foreign Application Priority Data

Aug. 12, 1992 [DE] Fed. Rep. of Germany ........ 4226657

[51] Int. Cl.$^5$ .......................... C12P 19/34; C12N 9/22
[52] U.S. Cl. ................................... 435/91.53; 435/199
[58] Field of Search ....................... 435/199, 91, 91.53

[56] References Cited

PUBLICATIONS

Shimotsu, H., et al., (1980) Agric. Biol. Chem., 44(7), 1665–1666.
Kessler, C., et al., (1990) Gene 92, 1, 96, 97.

*Primary Examiner*—Charles L. Patterson, Jr.
*Attorney, Agent, or Firm*—Felfe & Lynch

[57] ABSTRACT

The new type II restriction endonuclease SexAI has the following recognition sequence and preferably cleaves at the cleavage site defined by the mark:

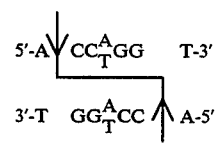

It is preferably obtainable from microorganisms of the genus Streptomyces.

10 Claims, No Drawings

TYPE II RESTRICTION ENDONUCLEASE SEXAI

FIELD OF THE INVENTION

The invention concerns the new type II restriction endonuclease SexAI, a process for its isolation and its use.

BACKGROUND AND PRIOR ART

Type II restriction endonucleases are endodeoxyribonucleases which are able to recognize and cleave particular DNA sequences. In this process, one phosphodiester bridge in each polynucleotide strand is hydrolyzed. Type II restriction endonucleases are thus of value for the analysis of DNA molecules. Although type II restriction endonucleases are known which are specific for numerous DNA sequences, there is still, however, a need for further type II restriction endonucleases which are specific for DNA sequences and which up to now are not recognized by any of the known restriction endonucleases. The object of the invention is therefore to provide a new restriction endonuclease which is able to specifically recognize and cleave a sequence which has not been recognized up to now by any such enzyme.

This object is achieved according to the present invention by a type II restriction endonuclease having the recognition sequence

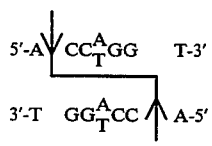

and the cleavage site indicated by the arrows.

DETAILED DESCRIPTION OF PREFERRED EMBODIMENTS

The new restriction endonuclease according to the present invention, which is denoted SexAI, has a temperature optimum at 37° C. The enzyme has good activity between pH 8.2 and pH 9.5 in 10 mmol/l Tris/HCl buffer with 1.0 mmol/l 2-mercaptoethanol, 5 mmol/l MgCl$_2$ and 100 mmol/l NaCl. The pH optimum is 9.2.

The recognition sequence can be confirmed by complete digestion of the DNAs of the SV40 and adeno 2 viruses, and the lambda phage (dcm−) and phage phiX174. These DNA molecules are treated with SexAI.

Table 1 shows a comparison of the cleavage site specificity observed experimentally with a cleavage site specificity determined by computer for an enzyme which recognizes the following sequence:

TABLE 1

| DNA | Number of cleavage sites determined experimentally | Number of cleavage sites determined by computer analysis | Fragment lengths (base pairs) determined experimentally | | Fragment lengths (base pairs) determined by computer analysis | | Cleavage positions determined by computer analysis (at base pair) | | |
|---|---|---|---|---|---|---|---|---|---|
| SV40 | 1 | 1 | 5243 | | 5243 | | 176 | | |
| phiX174 | 1 | 1 | 5386 | | 5386 | | 3499 | | |
| lambda | 5 | 5 | 22000 | 8700 | 22263 | 8745 | 22263 | 31008 | 32837 |
|  |  |  | 7700 | 4100 | 7659 | 4095 | 40496 | 44407 |  |
|  |  |  | 3900 | 1800 | 3911 | 1829 |  |  |  |
| ad2 | 9 | 9 | 14000 | 4000 | 13758 | 3917 | 3356 | 5658 | 6399 |
|  |  |  | 3400 | 3400 | 3369 | 3356 | 10316 | 11502 | 25260 |
|  |  |  | 3050 | 2400 | 3074 | 2389 | 28334 | 31703 | 34092 |
|  |  |  | 2300 | 1850 | 2302 | 1845 |  |  |  |
|  |  |  | 1200 | 750 | 1186 | 741 |  |  |  |

The cleavage position within the recognition sequence of the enzyme can be determined with a M13 derivative having this recognition sequence at a distance of ca. 30-200 bases from the binding site of the universal sequencing primer (Messing, J. et al., (1981) Nucl. Acids Res. 9, 309–321). First, sequencing reactions according to the dideoxy chain-termination method (Sanger, F. et al., (1977) Proc. Natl. Acad. Sci. USA 74, 560–564, Messing, J. et al., (1981) Nucl. Acids Res. 9, 309–321) are carried out on the single-stranded DNA of the M13 derivative using the universal sequencing primer.

Parallel to this, the sequencing primer is radioactively labelled at the 5' end with T4-polynucleotide kinase and [δ-$^{32}$P]ATP. After hybridization of this 5' end-labelled sequencing primer to the single-stranded M13 DNA, a partially double-stranded DNA is produced via a filling in reaction with DNA-polymerase I (Klenow enzyme) and a deoxynucleotide triphosphate mixture of dATP, dCTP, dGTP and dTTP. This DNA, the newly synthesized strand of which is radioactively labelled at the 5' end, is cleaved with the restriction endonuclease SexAI. Half of the cleavage preparation is again treated with T4 DNA polymerase in the presence of a mixture of all four deoxynucleotide triphosphates in order to obtain blunt DNA ends.

The analysis of the reaction products is carried out by electrophoresis on sequencing gels (8 mol/l urea, 5% polyacrylamide) and subsequent autoradiography. The results are interpreted according to Brown, N. L. and Smith, M. (Methods in Enzymology 65 (1980) 391–401). The position of the cleavage site is determined by a comparison of the distances of migration of the radioactively-labelled fragments with the sequencing ladder. The samples which were additionally treated with T4 DNA polymerase show a 5bp longer distance of migration of the bands compared to the sample which was only cleaved with SexAI. This therefore shows that SexAI produces a 5' DNA end which protrudes by 5bp. SexAI therefore cleaves within the recognition sequence with the following specificity:

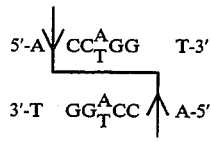

The number of cleavage sites determined experimentally is identical to the number of cleavage sites obtained by computer analysis with the different DNA's (Table I) for the sequence

In addition these data were also compared with the tables in Gene 92 (1990) 248.

SexAI is preferably produced by culturing microorganisms, especially Streptomyces, and isolating the enzyme from the cells. The strain *Streptomyces exfoliatus* is particularly preferred.

The microorganism *Streptomyces exfoliatus* has been deposited at the "Deutsche Sammlung von Mikroorganismen (DSM)", Mascheroder Weg 1b, 3300 Braunschweig, GFR and has the deposit number DSM 7194. The deposit was made on Jul. 27, 1992.

The usual biochemical methods of purification can be used for the isolation of the enzyme, wherein the presence of the enzyme in the respective fractions obtained can be easily tested on the basis of the cleavage of its recognition sequence. Lambda (dcm−) DNA e.g., is suitable as the substrate. The DNA fragments obtained are separated electrophoretically in agarose gels in buffer systems usually used for fragment separation in the presence of ethidium bromide.

The microorganisms used for the isolation of the enzyme grow aerobically in LB medium (10 g/l Bactotryptone, 5 g/l Bacto yeast extract and 10 g/l NaCl). The optimal conditions for growth are at 26° C., pH 6.5–7.5. The doubling time is about 2.5 hours.

The enzyme is isolated and purified by the usual chemical and mechanical methods such as by high pressure dispersion, ultrasound or enzymatic lysis. In a preferred embodiment of the process according to the present invention the cells are lysed by means of a French press. The further purification of the supernatant is preferably carried out by means of affinity chromatography and adsorption chromatography. Heparin-Sepharose CL-6B (Pharmacia) and Fractogel TSK AF Orange (Merck) are for example suitable as the material for the affinity chromatography. A suitable adsorption exchanger is for example HA Ultrogel (IBF).

The following examples elucidate the invention further.

EXAMPLE 1

A culture of microorganism *Streptomyces exfoliatus* is cultured for 10–12 hours at 26° C. and harvested at the end of the logarithmic growth phase. LB medium is used as the culture medium.

The cell paste (30 g wet weight) is resuspended in 2.4 volumes buffer A (40 mmol/l Tris-HCl, pH 8.0, 0.1 mmol/l EDTA, 7 mmol/l 2-mercaptoethanol) which contains protease inhibitors. Subsequently the cells are lysed by passing them through a French press at 23000 lb/inch² (two times), and then separating off the precipitate. NH₄Cl (final concentration 0.3 mol/l) is added to the supernatant. The nucleic acids are removed by a Polymin precipitation. Subsequently the centrifuged supernatant is dialyzed against buffer B (40 mmol/l Tris-HCl, pH 8.0; 0.1 mmol/l EDTA; 7 mmol/l 2-mercaptoethanol; 10% (w/v) glycerol) and fractionated over a heparin-Sepharose column. A gradient of 0.3–1 mol/l NaCl is used for the elution. SexAI is found in the fractions between 0.4 and 0.7 mol/l NaCl. The active fractions are equilibrated against buffer C (10 mmol/l potassium phosphate, pH 8.0; 0.1 mmol/l EDTA; 7 mmol/l 2-mercaptoethanol; 10% (w/v) glycerol) and fractionated on a HA-Ultrogel column. A gradient of 10–250 mmol/l potassium phosphate in buffer C is used for the elution. The active fractions are dialyzed against buffer B. Subsequently they are applied to a Fractogel TSK AF Orange column which has been equilibrated with buffer B. A gradient of 0.4–3 mol/l NaCl and 0.2% Thesit in buffer B is used for the elution.

The active fractions are pooled and dialyzed against storage buffer (20 mmol/l Tris-HCl, pH 8.0, 10 mmol/l 2-mercaptoethanol, 100 mmol/l NaCl, 0.1 mmol/l EDTA and 50% (v/v) glycerol).

EXAMPLE 2

Determination of Activity

Definition of the enzyme units: 1 U SexAI cleaves 1 μg lambda dcm−¹ DNA within 1 hour at 37° C. in 25 μl final volume.

17.9 μl water and 3.6 μl lambda dcm− DNA (optical density: 5.6OD/ml) as well as 1 μl SexAI solution (1 U/μl) are added to a mixture of 2.5 μl incubation buffer (100 mmol/l Tris-HCl, pH 8.0, 37° C., 50 mmol/l magnesium chloride, 1 mol/l NaCl and 10 mmol/l 2-ME). The solution is incubated for 1 hour at 37° C. cooled on ice and 5 μl of a terminating reagent consisting of 7 mol/l urea, 20% (w/v) sucrose, 60 mmol/l EDTA and 0.01% (w/v) bromophenol blue is added. Subsequently a separation is carried out by electrophoresis in 0.5% agarose gels for 3 - 4 hours at 100 V. The bands obtained are identified by comparison with a DNA length standard.

We claim:

1. Type II restriction endonuclease having recognition sequence

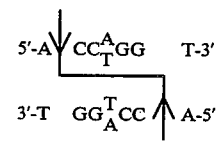

and a cleavage site indicated by the arrows.

2. The type II restriction endonuclease of claim 1, obtained from Streptomyces.

3. The type II restriction endonuclease of claim 1, obtained from *Streptomyces exfoliatus* DSM 7194.

4. The type II restriction endonuclease of claim 1, having a temperature optimum of 37° C. and a pH optimum of 9.2.

5. Process for obtaining the type II restriction endonuclease of claim 1, comprising culturing a sample of Streptomyces under conditions favoring production of said type II restriction endonuclease, and isolating said endonuclease therefrom.

6. The process of claim 5, wherein said Streptomyces is *Streptomyces exfoliatus* DSM 7194.

7. The process of claim 5, comprising lysing cells of said Streptomyces to form a supernatant, and isolating said endonuclease from said supernatant.

8. The process of claim 7, comprising isolating said endonuclease by subjecting said supernatant to affinity chromatography followed by adsorption chromatography.

9. The process of claim 8, comprising carrying out said affinity chromatography with carrier bound heparin.

10. Method for obtaining nucleotide sequence having a terminus selected from the group consisting of:

$$5'\text{-A-}3'$$
$$3'\text{-TGG}^A_T\text{CC-}5'$$

and $$5'\ \text{CC}^T_A\text{GGT-}3'$$
$$3'\text{-A-}5'$$

comprising contacting a DNA molecule with the type II restriction endonuclease of claim 1 under conditions favoring cleavage thereby, and isolating a cleavage product produced by action of said enzyme on said DNA molecule.

* * * * *